United States Patent
Nadolny et al.

(10) Patent No.: US 11,253,844 B2
(45) Date of Patent: Feb. 22, 2022

(54) OLIGOMERIZATION CATALYST AND PROCESS FOR THE PRODUCTION THEREOF

(71) Applicant: Evonik Operations GmbH, Essen (DE)

(72) Inventors: Fabian Nadolny, Arnsberg (DE); Stephan Peitz, Oer-Erkenschwick (DE); Guido Stochniol, Haltern am See (DE); Robert Franke, Marl (DE); Thomas Quandt, Marl (DE)

(73) Assignee: Evonik Operations GmbH, Essen (DE)

( * ) Notice: Subject to any disclaimer, the term of this patent is extended or adjusted under 35 U.S.C. 154(b) by 229 days.

(21) Appl. No.: 16/293,859

(22) Filed: Mar. 6, 2019

(65) Prior Publication Data

US 2019/0283004 A1 Sep. 19, 2019

(30) Foreign Application Priority Data

Mar. 14, 2018 (EP) .................................. 18161757

(51) Int. Cl.
| | | |
|---|---|---|
| B01J 23/755 | (2006.01) | |
| B01J 35/02 | (2006.01) | |
| B01J 35/10 | (2006.01) | |
| C07C 2/10 | (2006.01) | |
| B01J 35/00 | (2006.01) | |
| B01J 23/04 | (2006.01) | |
| B01J 37/02 | (2006.01) | |
| B01J 37/00 | (2006.01) | |
| B01J 21/12 | (2006.01) | |

(52) U.S. Cl.
CPC ............ *B01J 23/755* (2013.01); *B01J 23/04* (2013.01); *B01J 35/002* (2013.01); *B01J 35/026* (2013.01); *B01J 35/1019* (2013.01); *B01J 35/1061* (2013.01); *B01J 35/1076* (2013.01); *B01J 37/0009* (2013.01); *B01J 37/0063* (2013.01); *B01J 37/0201* (2013.01); *C07C 2/10* (2013.01); *B01J 21/12* (2013.01); *C07C 2521/12* (2013.01); *C07C 2523/04* (2013.01); *C07C 2523/755* (2013.01)

(58) Field of Classification Search
CPC ........ B01J 23/755; B01J 23/04; B01J 35/002; B01J 35/026; B01J 35/1019; B01J 35/1061; B01J 35/1076; B01J 37/0009; B01J 37/0063; B01J 37/0201; C07C 2/10
See application file for complete search history.

(56) References Cited

U.S. PATENT DOCUMENTS

| | | | |
|---|---|---|---|
| 3,557,242 A | 1/1971 | Sampson et al. | |
| 5,849,972 A | 12/1998 | Vicari et al. | |
| 6,733,657 B2 | 5/2004 | Benazzi et al. | |
| 7,572,946 B2 | 8/2009 | Lacombe et al. | |
| 7,939,597 B2 | 5/2011 | Bub et al. | |
| 8,198,481 B2 | 6/2012 | Kuppinger et al. | |
| 8,258,249 B2 | 9/2012 | Bub et al. | |
| 8,293,941 B2 | 10/2012 | Kuppinger et al. | |
| 8,481,784 B2 | 7/2013 | Kuppinger et al. | |
| 8,524,945 B2 | 9/2013 | Stochniol et al. | |
| 8,895,683 B2 | 11/2014 | Kuppinger et al. | |
| 9,676,805 B2 | 6/2017 | Dyballa et al. | |
| 9,845,276 B2 | 12/2017 | Franke et al. | |
| 9,856,184 B2 | 1/2018 | Stochniol et al. | |
| 10,155,200 B2 | 12/2018 | Geilen et al. | |
| 10,189,755 B2 | 1/2019 | Reeker et al. | |
| 10,196,327 B2 | 2/2019 | Stochniol et al. | |
| 2006/0276334 A1 | 12/2006 | Balduf et al. | |
| 2009/0068440 A1 | 3/2009 | Bub et al. | |
| 2013/0172599 A1* | 7/2013 | Suzuki ................. B01J 37/10 560/208 |
| 2016/0257634 A1 | 9/2016 | Dyballa et al. | |
| 2018/0072647 A1 | 3/2018 | Stochniol et al. | |
| 2018/0126361 A1 | 5/2018 | Klasovsky et al. | |

FOREIGN PATENT DOCUMENTS

| | | |
|---|---|---|
| DE | 10 2009 027408 A1 | 1/2011 |
| FR | 3 054 455 A1 | 2/2018 |
| JP | 2014151253 A1 | 8/2014 |
| TW | 200417555 A | 9/2004 |
| WO | 95/14647 A1 | 6/1995 |
| WO | 2014/123243 A1 | 8/2014 |

OTHER PUBLICATIONS

Nadolny et al., U.S. Appl. No. 16/293,702, filed Mar. 6, 2019.
Nadolny et al., U.S. Appl. No. 16/298,561, filed Mar. 11, 2019.
Nadolny et al., U.S. Appl. No. 16/293,859, filed Mar. 6, 2019.
German language European Search Report dated Aug. 29, 2019 in EP 19162229.9 (3 pages).
Moussa et al., "Heterogeneous oligomerization of ethylene to liquids on bifunctional Ni-based catalysts: The influence of support properties on nickel speciation and catalytic performance", Catalysis Today, Copyright Jan. 2016, Elsevier, Amsterdam, NL, Bd. 277, pp. 78-88 (11 pages).
Singapore Search Report completed on Jul. 27, 2021 in SG102019021345 (3 pages).
Fridag et al., U.S. Appl. No. 16/203,929, filed Nov. 29, 2018.
Fridag et al., U.S. Appl. No. 16/204,263, filed Nov. 29, 2018.
Fridag et al., U.S. Appl. No. 16/204,572, filed Nov. 29, 2018.
Nadolny et al., U.S. Appl. No. 16/291,144, filed Mar. 4, 2019.
Nadolny et al., U.S. Appl. No. 16/293,717, filed Mar. 6, 2019.

* cited by examiner

*Primary Examiner* — James A Fiorito
(74) *Attorney, Agent, or Firm* — Taylor English Duma LLP; Philip P. McCann

(57) ABSTRACT

The invention relates to an oligomerization catalyst comprising nickel oxide and silica-alumina support material and to a process for oligomerization of C3- to C6-olefins using the oligomerization catalyst.

10 Claims, No Drawings

OLIGOMERIZATION CATALYST AND PROCESS FOR THE PRODUCTION THEREOF

CROSS REFERENCE TO RELATED APPLICATIONS

This application is a 35 U.S.C. § 119 patent application which claims the benefit of European Application No. 18161757.2 filed Mar. 14, 2018, which is incorporated herein by reference in its entirety.

FIELD

The present invention relates to an oligomerization catalyst containing nickel oxide and a silica-alumina support material and to a process for producing the oligomerization catalyst. The present invention further relates to a process for oligomerization of C3- to C6-olefins using the oligomerization catalyst.

BACKGROUND

Oligomerization is generally understood as meaning the reaction of unsaturated hydrocarbons with themselves to form correspondingly longer-chain hydrocarbons, the so-called oligomers. Thus, for example, an olefin having six carbon atoms (hexene) can be formed by oligomerization of two olefins having three carbon atoms. The oligomerization of two molecules with one another is also referred to as dimerization.

The resulting oligomers are intermediates which may be used for example for the production of aldehydes, carboxylic acids and alcohols. The oligomerization of olefins is carried out on a large industrial scale either in the homogeneous phase using a dissolved catalyst or heterogeneously over a solid catalyst, or else with a biphasic catalyst system.

Among the heterogeneously catalysed processes, oligomerization over acidic oligomerization catalysts is long-established. Systems employed industrially include for example zeolites or phosphoric acid on a support. Isomeric mixtures of branched olefins are obtained here. For non-acidic, heterogeneously catalysed oligomerization of olefins with high dimer selectivity, nickel compounds on support materials are frequently employed in industry. Thus WO 95/14647 A1 describes a nickel catalyst comprising a support material consisting of the components titanium oxide and/or zirconium oxide, silicon dioxide and optionally aluminium oxide for olefin oligomerization. Over these catalysts, mixtures of linear butenes are oligomerized to $C_8$-olefins with a selectivity of below 75%.

WO 95/14647 A1 describes a process for oligomerization of olefins by means of an oligomerization catalyst which as active constituents after subtracting the loss on ignition after heat treatment at 900° C. comprises 10% to 70% by weight of nickel oxide, calculated as NiO, 5% to 30% by weight of titanium dioxide and/or zirconium dioxide, 0% to 20% by weight of aluminium oxide, 20% to 40% by weight of silicon dioxide and 0.01% to 1% by weight of an alkali metal oxide.

It is believed that the catalytic activity of nickel-based heterogeneous catalysts for the oligomerization of olefins, especially olefins having 3 to 6 carbon atoms, is based on the interaction between nickel cations and surface aluminium atoms. However, addition of titanium dioxide and/or zirconium dioxide has the result that the total composition has a lower percentage of aluminium/aluminium oxide which can result in the catalytic activity and/or the conversion being reduced. At the same time, the addition of titanium dioxide and/or zirconium dioxide may have the result that relatively large amounts of unwanted oligomerization products are formed, especially highly branched oligomers.

SUMMARY

It is accordingly an object of the present invention to provide an improved oligomerization catalyst which does not have the abovementioned disadvantages. It is a further object of the invention to provide an oligomerization catalyst which can achieve higher selectivities and higher conversions in the oligomerization without any negative effect on the service life of the catalyst and the mechanical properties such as strength.

The object of the present invention was achieved with the oligomerization catalyst according to claim 1 and the oligomerization process according to claim 8. Preferred embodiments are specified in the subsidiary claims.

DETAILED DESCRIPTION

The oligomerization catalyst according to the invention comprises nickel oxide, an Al-free and Si-containing binder (Al-free signifies: <0.1% by weight Al in the total composition of the binder), preferably silicon dioxide, and an amorphous silica-alumina support material, preferably an amorphous aluminosilicate. The binder is a material which ensures that the catalyst produced in accordance with the invention has the necessary mechanical strength. In the context of the present invention "x-ray-amorphous" is to be understood as meaning the property of a solid which results from the fact that it has no crystal structure, i.e. no long-range order. In the context of the present invention, however, it cannot be ruled out that the amorphous silica-alumina support material has small crystalline domains. The amorphous silica-alumina support material is therefore not a crystalline material, for example not a zeolitic material.

The oligomerization catalyst has a composition of 15% to 40% by weight, preferably 15% to 30% by weight, of NiO, 5% to 20% by weight of $Al_2O_3$, 55% to 80% by weight of $SiO_2$ and 0.01% to 1% by weight, preferably 0.05% to 0.5% by weight, of an alkali metal oxide, preferably sodium oxide. The figures are based on a total composition of 100% by weight. The oligomerization catalyst according to the invention moreover has a ratio of tetrahedral coordinated framework aluminium atoms to octahedral coordinated framework aluminium atoms in the range from 75:25 to 100:0, preferably in the range from 90:10 to 100:0, particularly preferably of 100:0, determined by $^{27}Al$ MAS NMR. The respective values for the octahedral and the tetrahedral coordination in the abovementioned ratio are to be understood as percentages based on the total number of the present aluminium atoms. In a particularly preferred embodiment of the present invention, the oligomerization catalyst is substantially free from titanium dioxide and/or zirconium dioxide, the oligomerization catalyst in particular comprising less than 0.5% by weight, preferably less than 0.1% by weight, particularly preferably less than 0.01% by weight, of titanium dioxide and/or zirconium oxide in its total composition.

The composition and coordinative properties of the oligomerization catalyst relate in particular to the state before employment in the oligomerization, i.e. the form in which the catalyst is charged into the reaction zone. The state of the catalyst, in particular of the surface atoms of the catalyst, cannot be conclusively determined during the oligomerization. However, in the present case the catalyst also exhibits a virtually identical composition and virtually identical coordinative properties after deinstallation from the reaction zone.

The ratio of the different coordinations of the aluminium atoms described here relates to all aluminium atoms in the silica-alumina support material, that is to say both bulk as well as surface atoms. The bulk structure of aluminosilicates typically consists of $SiO_4$ tetrahedra, $AlO_4$ tetrahedra and optionally also $AlO_6$ octahedra to a very small extent. However the outward-facing surface of this structure is missing the oxygen of an adjoining tetrahedron or octahedron. The silicon atom at the surface forms a silanol group relatively easily. The aluminium atom however formally has only a trivalent coordination with a free orbital. Including the free orbital, this corresponds to a tetrahedral coordination. The free orbital may undergo coordinative bonding with molecules or atoms, for example ammonia (ammonium form, structure I of the figure below) or to the oxygen of an adjacent silanol group (H form, structure II in the figure below). Due to the interaction between aluminium and the adjacent oxygen, the OH bond of the adjacent silanol group is weakened and the OH group can function as a proton donor. With water from the ambient air the oxygen from the water molecules bonds coordinatively to the aluminium atom as an electron donor. Three water molecules may become attached, thus forming an octahedral coordination (see structure III in the figure below).

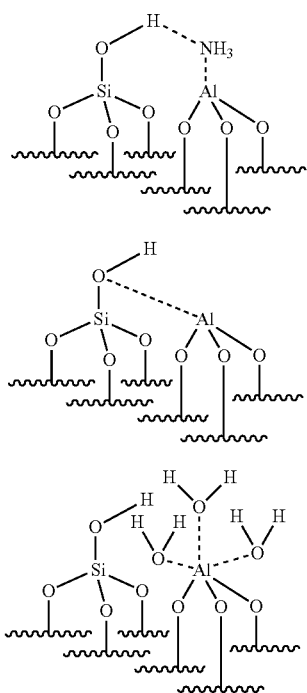

The coordinative properties of the aluminium atoms of the oligomerization catalyst have an influence on the oligomerization. In the prior art the focus is especially on a predominantly octahedral coordination of the aluminium atoms, such as is described in U.S. Pat. No. 7,572,946 B2 or U.S. Pat. No. 6,733,657 B2. In the present case, it has surprisingly been found, however, that by adjusting the ratio of tetrahedrally coordinated and octahedrally coordinated framework aluminium atoms to values in the range from 75:25 to 100:0, preferably in the range from 90:10 to 100:0, particularly preferably of 100:0, it is possible to achieve particularly good catalyst properties, such as a higher conversion and/or a higher selectivity, when using the oligomerization catalyst according to the invention.

The ratio of tetrahedrally coordinated aluminium atoms to octahedrally coordinated aluminium atoms can be determined by $^{27}Al$ MAS NMR, wherein the tetrahedral coordination of the aluminium atoms is detected at 50 to 60 ppm and the octahedral coordination of the aluminium atoms is detected at 0 ppm and these coordinations may be evaluated by integration of the peaks. The precise measurement of the NMR spectra was performed as follows: This initially comprises sample preparation where the samples to be investigated are stored for about 2 hours in an atmosphere saturated with water vapor prior to analysis (desiccator, samples at room temperature 2 to 3 cm above distilled water). As a result, the signal intensity is increased and it is ensured that all samples have the same starting point. Following this, 300 to 500 mg of sample material, according to the density, are placed in a $ZrO_2$ solid state spinner (external diameter 4 mm) and compacted with slight pressure.

The actual NMR measurements are carried out on a Bruker 400 Avance III HD spectrometer with a special solid state sample head. To eliminate anisotropy, for solid-state samples the samples are inclined at about 54° and set into rapid rotation (for $^{27}Al$ e.g. 12 kHz). A simple 90° pulse is used for signal excitation. Owing to the very rapid relaxation of $^{27}Al$ nuclei, measurements are taken with a very short delay of about 50 ms so that a very rapid pulse sequence is possible. The sweep width is 400 ppm, wherein the sender is set to 0 ppm (measurement range +200 to −200 ppm).

The evaluation of the spectra is carried out as follows: Solid state spectra of quadropole nuclei ($^{27}Al$ is a quadrupole nucleus (nuclear spin I=5/2)) often have baselines that are difficult to correct. Baseline correction using a polynomial is in most cases suitable for this purpose once phase correction has been carried out. The rotation side bands appearing at equidistant spacings (spacing 12 kHz) are outside the evaluation range and thus do not affect the evaluation. The relevant signals are integrated taking account of the respective line widths and may be related to one another to determine the percentage proportions (% Al). The spectra are referenced to a saturated $Al(NO_3)_3$ solution ($\delta$=0.0 ppm). A tetrahedral coordination of the aluminium atoms is detected in the NMR spectrum range from 50 to 60 ppm. An octahedral coordination of the aluminium atoms generates a peak around 0 ppm in the NMR spectrum.

According to the invention the oligomerization catalyst may additionally have a specific surface area (calculated according to BET) of 150 to 400 m$^2$/g, preferably 190 to 350 m$^2$/g, particularly preferably of 220 to 330 m$^2$/g. The specific surface area is measured by nitrogen physisorption according to DIN ISO 9277 (2014-01 version) or calculated therefrom.

In a further preferred embodiment the oligomerization catalyst comprises mesopores and macropores, i.e. has a bimodal pore size distribution. The mesopores of the oligomerization catalyst according to the invention have an average pore diameter of 5 to 15 nm, preferably of 7 to 14 nm, particularly preferably of 9 to 13 nm. By contrast the macropores of the oligomerization catalyst according to the invention preferably have an average pore diameter of 1 to 100 μm, particularly preferably of 2 to 50 μm. The average pore volume of the oligomerization catalyst according to the invention, i.e. of both the mesopores and the macropores, may be 0.5 to 1.5 cm$^3$/g, preferably 0.7 to 1.3 cm$^3$/g. The average pore diameter and the average pore volume may be determined by mercury porosimetry according to DIN 66133 (1993-06 version).

The oligomerization catalyst according to the invention is preferably present as granulate. Furthermore the oligomerization catalyst according to the invention may have an average particle diameter (d50) of 0.1 mm to 7 mm, preferably 0.5 to 6 mm, particularly preferably of 1 mm to 5 mm. The average particle diameter may be determined by imaging methods, in particular by the methods mentioned in the standards ISO 13322-1 (2004 Dec. 1 version) and ISO 13322-2 (2006 Nov. 1 version). A suitable instrument for analysis of particle diameter is for example the Camsizer 2006 instrument (Retsch Technology).

In a further preferred embodiment the oligomerization catalyst has a bulk crush strength (BCS) of more than 0.5 MPa, preferably of more than 0.6 MPa and particularly preferably of more than 0.8 MPa. The BCS value is a measure of the mechanical strength of mineral granulates. The bulk crush strength (BCS) of a solid is to be understood as meaning a parameter defined as a pressure in MPa at which 0.5% by weight of fines fraction (i.e. particles screened off using a screen with a mesh size of 0.425 mm) are formed when the solid sample is subjected to pressure via a piston in a tube. For this purpose 20 ml of the solid are prescreened with a screen (mesh size: 0.425 mm), filled into a cylindrical sample tube (internal diameter: 27.6 mm, wall thickness: 5 mm, height: 50 mm) and 5 ml of steel spheres (diameter: 3.9 mm) are placed on the top surface of the solid. The solid is subsequently subjected to different (increasing) pressures for three minutes. The fines fractions formed by the subjection to pressure are then removed by screening, in each case weighed as a sum total and the percentage fraction thereof is determined. This process is performed until an amount of 0.5% by weight of fines fraction is reached.

An oligomerization catalyst may also be characterized by means of its maximum poured density. In a preferred embodiment the oligomerization catalyst according to the invention has a maximum poured density of 0.1 to 2 g/cm$^3$, preferably 0.2 to 1.5 g/cm$^3$, particularly preferably of 0.3 to 1.0 g/cm$^3$. Determination of poured density may be carried out via a measuring cylinder. The measuring cylinder is filled with a certain volume of the solid to be investigated, for example via a suitable metering apparatus such as the DR100 apparatus (Retsch) and the measuring cylinder is weighed. The maximum poured density may be determined from the weight and the volume. It may be necessary to subtract the residual moisture from the sample weight.

The oligomerization catalyst according to the invention is produced by a process comprising the steps of:
a) mixing the amorphous silica-alumina support material and the Al-free and Si-containing binder optionally also with at least a portion of a nickel source, and granulating the thus-produced mixture;
b) treating (impregnating) the granulate produced in step a) with at least a portion of a nickel source provided that the entirety of the nickel source has not already been mixed with the silica-alumina support material and the amorphous Al-free and Si-containing binder in step a); and
c) calcining the granulate to produce the oligomerization catalyst.

The amorphous silica-alumina support material employed in step a) comprises in the calcined state (without Ni) a ratio of tetrahedral coordinated framework aluminium atoms to octahedral coordinated framework aluminium atoms of 50:50 to 74:26, preferably 55:45 to 70:30. The ratio of coordination of tetrahedral coordinated framework aluminium atoms to octahedral coordinated framework aluminium atoms in the silica-alumina support material therefore differs from the same ratio in the final oligomerization catalyst and thus changes during the production of the catalyst. The proportion of the tetrahedral coordination in the stated ratio will increase from the employed silicon-alumina support material to the final oligomerization catalyst while the proportion of the octahedral coordination falls.

The amorphous silica-alumina support material is an amorphous aluminosilicate comprising 10% to 20% by weight, preferably 12% to 17% by weight, of $Al_2O_3$ and 80% to 90% by weight, preferably 83% to 88% by weight, of $SiO_2$. This relates to the composition without any sorbed compounds (for example water or ammonia) which are for example reported under the term loss on ignition in commercially available products. In a preferred embodiment the amorphous aluminosilicate employed as the silica-alumina support material may have a particle size (d50) in the range from 10 to 80 μm, preferably 15 to 75 μm. The amorphous aluminosilicate employed as the silica-alumina support material moreover preferably has a specific surface area (calculated as BET) of 290 to 380 m$^2$/g, particularly preferably of 300 to 360 m$^2$/g, measured by nitrogen physisorption according to DIN-ISO 9277 (2014-01 version). The proportion of the silica-alumina support material in the total batch (total composition including any and all employed solvents such as water) in step a) is 20% to 60% by weight, preferably 25% to 50% by weight, when the entirety of the nickel source is already added in step a). When the nickel source is partially or completely added only in step b) a sufficient amount of liquid to allow granulation should be added to the mixture in step a) by addition of a solvent, preferably water or an ammoniacal solution.

The Al-free and Si-containing binder likewise employed in step a) (Al-free signifies: <0.1% by weight of Al in the total composition of the binder) is preferably silicon dioxide. The Al-free and Si-containing binder is moreover preferably present not in solid form but rather in the form of a colloidal dispersion, particularly preferably a silica sol. In a preferred embodiment the solvent in which the Al-free and Si-containing binder, preferably the silicon dioxide, is present in dispersed form is water, the dispersion preferably additionally containing ammonia for stabilization. The Al-free and Si-containing binder, preferably the silicon dioxide, is present in the dispersion in an amount in the range from 7% to 50% by weight, preferably 12% to 42% by weight, particularly preferably 20% to 35% by weight. The average particle size of the Al-free and Si-containing binder, preferably of the silicon dioxide, may be 5 to 20 nm, preferably 6 to 10 nm, particularly in the dispersion (determinable by light scattering methods). The viscosity of the dispersion comprising the Al-free and Si-containing binder, preferably the silicon dioxide, may be in the range from 1 to 50 mPas, preferably 5 to 25 mPas. The dispersion comprising the Al-free and Si-containing binder, preferably the silicon dioxide, may further preferably have a pH in the range from 7 to 12, preferably 8 to 10. The density of the dispersion comprising the Al-free and Si-containing binder, preferably the silicon dioxide, is preferably 1 to 1.3 g/cm$^3$, particularly preferably 1.1 to 1.25 g/cm$^3$. The proportion of the Al-free and Si-containing binder in the total batch (total composition including any and all employed solvents such as water) in step a) and optionally b) is 0.5% to 15% by weight, preferably 1% to 10% by weight.

No separate alkali source is added to the mixture in step a) or b). The content of alkali metal oxide derives from the silica-alumina support material and/or the Al-free and Si-containing binder which may contain small amounts of alkali metals, in particular sodium. The alkali contents of support material and binder are to be chosen such that they do not fall short of a proportion of 0.01% by weight and do not exceed a proportion of 1% by weight.

The nickel source employed in step a) or b) is a solution of a nickel compound, a paste of a nickel compound or a solution and a paste, wherein in principle any soluble nickel compound can be employed. Included among these are nickel nitrate ($Ni(NO_3)_2$), nickel acetate ($Ni(ac)_2$), nickel acetylacetonate ($Ni(acac)_2$), nickel sulfate ($NiSO_4$), nickel citrate or nickel carbonate ($NiCO_3$). Preference is given to nickel nitrate ($Ni(NO_3)_2$), nickel sulfate ($NiSO_4$) or nickel carbonate ($NiCO_3$). The nickel solution is an aqueous or ammoniacal solution. An ammoniacal solution is an aqueous solution admixed with ammonia. The nickel paste contains water and the nickel paste according to the present invention contains less water than the nickel solution (when the same amount of nickel compound is assumed). Nickel paste is in principle a moistened solid composed of a nickel compound which is incompletely hydrated and in which hydroxidic nickel compounds are formally also formed; in the case of nickel carbonate for example $NiCO_3*Ni(OH)_2$ but also non-stoichiometric nickel carbonate hydroxides. In a preferred embodiment the nickel paste contains between 30% and 50% by weight, preferably 35% to 45% by weight, of nickel based on the total weight of the paste. The nickel solution may contain nickel in an amount in the range from 1% to 20% by weight, preferably 5% to 15% by weight, in each case based on the total weight of the solution.

In a preferred embodiment the nickel solution employed is an ammoniacal $Ni(CO_3)$ solution, known as NiHAC solution (a nickel hexamine carbonate complex is formed in the solution ($[Ni(NH_3)_6]CO_3$)) which has a nickel content in the range from 1% to 20% by weight, preferably 5% to 15% by weight. Employable as the nickel paste is a paste composed of nickel carbonate and water as solvent, wherein the nickel is present as carbonate/hydroxide (general empirical formula $NiCO_3*Ni(OH)_2$ but nonstoichiometric nickel carbonate hydroxides may also be formed). The paste may have a nickel content in the range from 30% to 50% by weight, preferably 35% to 45% by weight. In a particularly preferred embodiment the production of the oligomerization catalyst employs in step a) and/or in optional step b) a NiHAC solution.

The total amount of nickel source (paste and/or solution) in the total batch (total composition of any and all employed solvents such as water) in step a) and optionally b) of the production process is between 40% and 70% by weight, preferably 45% and 65% by weight.

The process according to the invention has the particular feature that in step a) no titanium dioxide and no zirconium dioxide are added to the mixture but rather the oligomerization catalyst is produced without addition of titanium dioxide and zirconium oxide. Any incidences of titanium dioxide and/or zirconium dioxide in the total composition of the oligomerization catalyst are due to impurities/trace incidences in the employed components.

In step a) the individual components, i.e. the silica-alumina support material, the Al-free and Si-containing binder and optionally the nickel source, are mixed with one another in a mixing vessel using an agitator and simultaneously or subsequently granulated. This may be effected using an intensive mixer for example. Mixing and granulation may typically be performed at ambient pressure. The temperature at which mixing and granulation may be carried out is preferably in the range from 10° C. to 60° C. The duration of process step a), i.e. of mixing and granulation, is between 5 minutes and 1 hour, preferably between 10 and 30 minutes.

In optional step b) the remaining portion of the nickel source, preferably in the form of a NiHAC solution, is added to the granulate produced in step a) and mixed with the granulate in order to treat the granulate with nickel. If at least a portion of the nickel source is to be added in step b) the possibly moist granulate from step a) may be dried prior to the treatment with the nickel source. The drying temperature may be 80° C. to 250° C., preferably 100° C. to 220° C.

The nickel source causes a nickel compound to be deposited on the surface of the silica-alumina support material. As a result at least some of the previously octahedral coordinated aluminium atoms at the surface are fixed in a tetrahedral coordination and after calcination can no longer assume an octahedral coordination. The binder is added as the substance which joins the different materials and is Al-free here to ensure that no additional octahedrally coordinated aluminium atoms are introduced into the catalyst. Any octahedrally coordinated aluminium atoms in the bulk of the support material remain untouched thereby as a result of which even after mixing with the binder a certain amount of octahedrally coordinated aluminium atoms may be present in the finished oligomerization catalyst.

The granulate resulting from step a) and/or step b) may still contain at least a portion of the employed solvent, in particular water. A moist granulate may therefore be concerned. Before the possibly still moist granulate is subjected to the calcination in step c) the moist granulate may be screened, preferably with a screen having a mesh size of 0.1 to 1.5 mm. The screened-off portion of the granulate (undersize) may be recycled back to step a) of the granulation.

After the mixing and granulating in step a), optionally after the treating (impregnating) of a granulate with at least a portion of a nickel source in step b) and optionally after the screening of the moist granulate the granulate may initially be dried in step c). This may be effected using known apparatuses such as for example belt dryers or the like. The drying temperature may be in the range from 80° C. to 250° C., preferably in the range from 100° C. to 220° C.

Before the optionally dried granulate is subjected to the calcination the dried granulate may be fractionated in order to establish a particular particle size of the granulate. Such a fractionation may be achieved for example through the use of at least one screen having a defined mesh size. In a particularly preferred embodiment two screens are used, wherein the one screen has a mesh size of 0.1 to 1.5 mm and the other screen has a mesh size of 2.5 to 7 mm. The remaining fractions (oversize and undersize) may be recycled to step a) optionally after preceding milling.

The optional drying and possible fractionation of the granulate is followed by the calcination of the granulate. This may comprise heating the granulate in a suitable furnace, preferably in a nitrogen stream, particularly preferably in a nitrogen countercurrent. Air may be added to the nitrogen stream during the calcination, wherein the amount of air supplied may be 100 to 10 000 ppm by volume, preferably 300 to 7000 ppm by volume. The calcination temperature may be 400° C. to 900° C., preferably 450° C. to 700° C., particularly preferably 500° C. to 600° C. This temperature may be maintained over several hours, preferably 5 to 20 hours, particularly preferably 8 to 15 hours, before the granulate is cooled. Air may be introduced into the furnace during cooling but the amount of air introduced should be controlled. The amount of the air optionally supplied is 100 to 10 000 ppm by volume, preferably 300 to 7000 ppm by volume.

The cooled granulate/the finished oligomerization catalyst may possibly then be fractionated once again to establish a particular particle size of the cooled granulate. Such a fractionation may be achieved for example through the use of at least one screen having a defined mesh size. In a particularly preferred embodiment two screens are used, wherein one screen has a mesh size of 0.1 to 1.5 mm and the other screen has a mesh size of 2.5 to 7 mm. The remaining fractions (oversize and undersize) may be recycled to step a) optionally after preceding milling.

After the last process step, of calcination and subsequent fractionation after cooling, the thus-produced oligomerization catalyst has a final total composition of 15% to 40% by weight, preferably 15% to 30% by weight, of NiO, 10% to 30% by weight of $Al_2O_3$, 55% to 70% by weight of $SiO_2$ and 0.01% to 1% by weight, preferably 0.05% to 0.5% by weight, of an alkali metal oxide. The figures are based on a total composition of 100% by weight.

A reduction in conversion and/or selectivity during oligomerization may be encountered with increasing employment time of the oligomerization catalyst. The catalyst according to the invention may be regenerated after use in the oligomerization reaction.

Regeneration of the oligomerization catalyst comprises the steps of:
d) burnoff; and
e) restoration of the active surface structure of the oligomerization catalyst.

After use in oligomerization reactions the oligomerization catalyst may exhibit deposits of organic substances that require removal. Removal of the organic compounds deposited in the catalyst is preferably accomplished in step d) by burnoff (oxidation) to form carbon oxides and water. The burnoff step d) may be performed continuously or discontinuously in a furnace, for example in a rotary kiln or a shaft furnace. For this purpose the oligomerization catalyst (in the form of a granulate) is supplied to the furnace and preferably maintained at a predetermined furnace temperature of 400° C. to 600° C., particularly preferably of 500° C. to 600° C. The combustion air used during burnoff is supplied in countercurrent and in addition further air is optionally blown into the granulate (oligomerization catalyst) via suitable inlets to ensure rapid burnoff.

Step e), i.e. the restoration of the active surface structure of the oligomerization catalyst may in a step e1) comprise an (additional) treatment (impregnation) with nickel. The treatment with nickel may be effected analogously to the production of the oligomerization catalyst (step b)) but optionally with the difference that a nickel solution having a lower nickel concentration than in the production of the oligomerization catalyst may be used. A nickel paste is typically not employed in the regeneration. The aim here is to deposit additional amounts of nickel on the oligomerization catalyst. In principle any soluble nickel compound such as nickel nitrate ($Ni(NO_3)_2$), nickel acetate ($Ni(ac)_2$), nickel acetylacetonate ($Ni(acac)_2$), nickel sulfate ($NiSO_4$) or nickel carbonate ($NiCO_3$) may be used therefor to produce an aqueous or ammoniacal nickel solution.

The use of NiHAC solutions obtainable by dissolving nickel carbonate ($NiCO_3$) in concentrated ammonia solutions, optionally with addition of ammonium carbonate, has proven particularly advantageous. Such solutions may be used for the impregnation with nickel contents of 0.5 to 14% by weight, in particular of 2 to 10% by weight, very particularly of 4 to 8% by weight.

For nickel application the oligomerization catalyst burned off in step d) is for example impregnated with a NiHAC solution having nickel contents of 0.5 to 14% by weight, in particular of 2% to 10% by weight, very particularly of 4% to 8% by weight until saturation of the pores. The impregnation may be performed with a process familiar to those skilled in the art such as for example by spraying until permanent appearance of a liquid film on the surface (incipient wetness). If the solution takeup is about 0.8 to 1.2 g of solution per g of oligomerization catalyst a deposition of about 0.5% to 6% by weight of additional nickel in the form of a basic carbonate can be achieved.

If the oligomerization catalyst is subjected to a step e1), i.e. treated with nickel, the oligomerization catalyst should be dried in a suitable drying apparatus, for example a belt dryer with an air stream or else a conical dryer, at temperatures between 80° C. and 250° C., preferably between 100° C. and 220° C., and at standard pressure or else under vacuum.

Step e) comprises at least the step e2), the calcination that would be performed after an optional step e1). The calcination of the oligomerization catalyst may be performed continuously or discontinuously in a suitable furnace, for example a shaft furnace or rotary kiln. In the case of a continuous calcination in step e2) it is furthermore preferable when a gas continues to be passed through the oligomerization catalyst (granulate) in countercurrent. The gas employed may be air, nitrogen or a mixture thereof. The gas stream may be 0.2 to 4 $m^3$ of gas per kg of granulate and hour and the inlet temperature of the gas may be from 400° C. to 800° C., preferably 450° C. to 700° C. In addition to this heat introduced via the gas, energy may be introduced by active heating of the walls of the furnace.

The calcination temperature in the furnace may be 400° C. to 800° C., preferably 450° C. to 700° C., particularly preferably 500° C. to 600° C. This temperature may be maintained over several hours, preferably 5 to 60 hours, particularly preferably 10 to 40 hours, before the granulate is cooled. Cooling is preferably carried out in a nitrogen stream. Nitrogen may additionally be added to the air and the amount of air should preferably be controlled. The amount of air preferably added to the nitrogen may be 100 to 10 000 ppm by volume, preferably 300 to 7000 ppm by volume.

The oligomerization catalyst according to the invention/a catalyst produced or regenerated by the process according to the invention may be used in particular for the oligomerization of C3- to C6-olefins, preferably C3- to C5-olefins, particularly preferably C4-olefins, or olefin-containing input mixtures based thereupon. The olefins or olefin-containing input mixtures are employed as a reactant stream.

The present invention also provides a process for oligomerization of C3- to C6-olefins, wherein olefin-containing input mixture which contains the C3- to C6-olefins is passed over a catalyst in at least one reaction zone, wherein the oligomerization catalyst according to the invention is used to catalyse the oligomerization reaction. According to the invention, a reaction zone comprises at least one reactor and at least one distillation column in which the formed oligomers can be separated. The process according to the invention can also be operated with two or more reaction zones. The oligomerization preferably takes place in the liquid phase.

Olefins employed for the process according to the invention include C3- to C6-olefins, preferably C3- to C5-olefins, particularly preferably C4-olefins, or olefin-containing input mixtures based thereupon which may also contain proportions of analogous alkanes. Suitable olefins are inter alia α-olefins, n-olefins and cycloalkenes. The olefins used as reactants are preferably n-olefins. In a particularly preferred embodiment, the olefin is n-butene. According to the invention the term "olefin-containing input mixtures based thereupon" is to be understood as encompassing any type of mixtures containing the relevant C3- to C6-olefins to be oligomerized in an amount which makes it possible to perform the oligomerization. Olefin-containing input mixtures preferably contain virtually no further unsaturated compounds and polyunsaturated compounds such as dienes or acetylene derivatives. It is preferable to employ olefin-containing input mixtures containing less than 5% by weight, in particular less than 2% by weight, of branched olefins based on the olefin proportion. Olefin-containing input mixtures which contain less than 2% by weight of branched olefins, in particular iso-olefins, are further preferably employed.

Propylene (C3) is produced on a large industrial scale by cracking of naphtha and is a commodity chemical which is readily available. $C_5$-olefins are present in light petroleum fractions from refineries or crackers. Industrial mixtures containing linear $C_4$-olefins include light petroleum fractions from refineries, $C_4$-fractions from FC crackers or steam crackers, mixtures from Fischer-Tropsch syntheses, mixtures from the dehydrogenation of butanes, and mixtures formed by metathesis or from other industrial processes. Mixtures suitable for the process according to the invention are obtainable for example from the $C_4$-fraction of a steam cracker. Butadiene is removed in the first step here. This is accomplished either by extraction or extractive distillation of the butadiene or by selective hydrogenation thereof. In both cases a virtually butadiene-free $C_4$-cut is obtained, namely raffinate 1. In the second step, isobutene is removed from the $C_4$-stream, for example by production of methyl tert-butyl ether (MTBE) by reaction with methanol. Other options include the reaction of the isobutene from the raffinate I with water to afford tert-butanol or the acid-catalysed oligomerization of isobutene to afford diisobutene. The now isobutene-free $C_4$-cut, raffinate II, contains, as desired, the linear butenes and possibly butanes. The 1-butene may optionally still be removed by distillation. Both fractions, the one comprising but-1-ene or the one comprising but-2-ene, may be used in the process according to the invention.

In a further preferred embodiment $C_4$-olefin-containing material streams are supplied to the process as an olefin-containing input mixture. Suitable olefin-containing input mixtures are inter alia raffinate I (butadiene-free C4-cut from the steam cracker) and raffinate II (butadiene-free and isobutene-free C4-cut from the steam cracker).

A further option for producing a suitable olefin-containing input mixture is that of subjecting raffinate I, raffinate II or a similarly constituted hydrocarbon mixture to hydroisomerization in a reactive column. This may include inter alia a mixture consisting of 2-butenes, small proportions of 1-butene and possibly n-butane and also isobutane and isobutene.

The oligomerization is generally carried out at a temperature in the range from 50° C. to 200° C., by preference 60° C. to 180° C., preferably in the range from 60° C. to 130° C., and at a pressure of 10 to 70 bar, preferably of 20 to 55 bar. If the oligomerization is to be carried out in the liquid phase the parameters pressure and temperature must to this end be chosen such that the reactant stream (the employed olefins or olefin mixtures) is in the liquid phase. The weight-based space velocities (reactant mass per unit catalyst mass per unit time; weight hourly space velocity (WHSV)) of the olefin-containing input mixture are in the range between 1 g of reactant per g of catalyst and per h (=1 $h^{-1}$) and 190 $h^{-1}$, preferably between 2 $h^{-1}$ and 35 $h^{-1}$, particularly preferably between 3 $h^{-1}$ and 25 $h^{-1}$.

In one embodiment, the degree of dimerization (also referred to as "percentage selectivity based on dimerization") after the oligomerization based on the converted reactant is at least 60%, more preferably at least 75%, particularly preferably at least 80%.

The linearity of an oligomerization product/of the dimers formed is described by the ISO index and represents a value for the average number of methyl branches in the dimer. Thus (for butene as the reactant) n-octenes contribute 0, methylheptenes contribute 1 and dimethylhexenes contribute 2 to the ISO index of a C8 fraction. The lower the ISO index, the more linear the construction of the molecules in the respective fraction. The ISO index is calculated according to the following general formula:

$$\frac{(\text{singly branched dimers (\% by weight)} + 2 \times \text{doubly branched dimers (\% by weight)})}{(100)}$$

Accordingly a dimer mixture having an ISO index of 1.0 has on average precisely 1 methyl branch per dimeric molecule.

The ISO index of the product from the oligomerization process according to the invention is preferably 0.8 to 1.2, particularly preferably 0.8 to 1.15.

The oligomers produced by the process according to the invention are utilized inter alia for producing aldehydes, alcohols and carboxylic acids. Thus for example the dimerisation of linear butenes affords a nonanal mixture by hydroformylation. This provides either the corresponding carboxylic acids by oxidation or a $C_9$-alcohol mixture by hydrogenation. The $C_9$-acid mixture may be used for producing lubricants or siccatives. The $C_9$-alcohol mixture is a precursor for the production of plasticizers, particularly dinonyl phthalates, or DINCH.

Even without further elaboration it is assumed that a person skilled in the art will be able to utilize the description above to the greatest possible extent. The preferred embodiments and examples are therefore to be interpreted merely as a descriptive disclosure which is by no means limiting in any way whatsoever.

The present invention is more particularly elucidated hereinbelow with reference to examples. Alternative embodiments of the present invention are obtainable analogously.

Example

Catalyst Synthesis (Inventive Catalyst 1):

Placed into the mixing vessel of an intensive mixer are a binder (colloidal solution comprising silicon dioxide, $SiO_2$ content of about 30% by weight), a nickel source (NiHAC solution, nickel content between 11% to 12.5% by weight) and amorphous silica-alumina (77.2% by weight $SiO_2$, 12.2% by weight $Al_2O_3$, remainder: water, ammonia, traces of further oxides (loss on ignition), average particle size of 22 µm, specific surface area of 320 $m_2/g$), ratio of tetrahedrally coordinated framework aluminium atoms to octahedral coordinated framework aluminium atoms of 65:35 (calcined without Ni)).

Once all components have been added the mixture is stirred at a relatively low speed to ensure effective distribution. A subsequent increase in the speed of the stirrer brings about a slow densification and granulation of the composition. Stirring is stopped as soon as granulates having a suitable particle diameter (0.1 mm to 7 mm) are obtained. The thus obtained granulate is dried at about 120° C. and subsequently screened using two screens to remove from the granulate excessively small or excessively large particles.

The granulate is then calcined in a furnace. For the calcination the granulate is heated to a temperature between 500° C. to 600° C. and this temperature is maintained for about 10 to 12 hours. The furnace filled with granulate has nitrogen flowing through it and a ratio of volumes of granulate to volumes of nitrogen per hour (standard volumes) of at least 1:1000 is maintained. During the cooling of the granulate to room temperature about 6000 ppm by volume of air are metered into the nitrogen stream. The cooled granulate corresponds to the finished oligomerization catalyst. The thus-produced catalyst has a ratio of tetrahedral coordinated framework aluminium atoms to octahedral coordinated framework aluminium atoms of about 95:5.

Catalyst Synthesis (Noninventive Catalyst 2):

Placed into the mixing vessel of an intensive mixer are a binder (solution composed of boehmite and a 1% by weight nitric acid solution, aluminium content between 15% to 17% by weight), a nickel source (nickel paste, moistened nickel carbonate, nickel content between 40% to 42% by weight) and amorphous silica-alumina (77.2% by weight $SiO_2$, 12.2% by weight $Al_2O_3$, remainder: water, ammonia, traces of further oxides (loss on ignition), average particle size of 22 µm, specific surface area of 320 m$_2$/g, ratio of tetrahedrally coordinated framework aluminium atoms to octahedral coordinated framework aluminium atoms of 65:35 (calcined without Ni)).

The silica-alumina, the binder and the solid nickel source are mixed in the intensive mixer. During the commixing additional liquid components comprising a NiHAC solution (nickel carbonate dissolved in concentrated ammoniacal solution, nickel content between 11% and 12.5%) and an alkali metal compound (sodium carbonate dissolved in distilled water) are slowly added into the mixing vessel via a funnel.

The rest of the production, comprising granulation, drying, screening and calcination, corresponds to the production for catalyst 1. The thus-produced catalyst has a ratio of tetrahedral coordinated framework aluminium atoms to octahedral coordinated aluminium atoms of approximately 65:35.

Use of the Catalysts in the Oligomerization:

In each case about 12 g of the catalyst were filled into a metal tube having an internal diameter of 6 mm. Placed in front of and behind the catalyst were glass pearls having a diameter of 2 mm which serve as a pre-heating/cooling phase. The oligomerization was performed using a feed stream at 30 bar and a loading of 7.5 g/h of butene per gram of catalyst, wherein the reaction temperature was varied between 80° C. and 100° C. The products were analysed by gas chromatography for the conversion of butenes and the linearity of the octenes. The compositions of the feed stream for the oligomerization are shown in table 1 which follows.

The conversions and selectivities achieved for the feed stream as a function of temperature for catalyst 1 (inventive) and catalyst 2 (noninventive) and the ISO indices resulting therefrom are reported in tables 2 and 3.

TABLE 1

Composition of feed stream
Feed stream

| | |
|---|---|
| isobutane | 8.0% |
| n-butane | 15.3% |
| trans-2-butene | 27.9% |
| 1-butene | 32.7% |
| isobutene | 0.9% |
| cis-2-butene | 15.2% |

TABLE 2

Conversions and ISO indices in oligomerization using catalyst 1
Loading (Feed of C4-olefins in g/h per unit mass of catalyst in g) as WSHV: 7.5 h$^{-1}$

| | Temperature | Conversion based on C4-olefins | ISO index |
|---|---|---|---|
| Catalyst 1 (inventive) | 80° C. | 36.2% | 1.09 |
| | 90° C. | 41.6% | 1.12 |
| | 100° C. | 44.9% | 1.10 |

TABLE 3

Conversions and ISO indices in oligomerization using catalyst 2
Loading (Feed of C4-olefins in g/h per unit mass of catalyst in g) as WSHV: 7.5 h$^{-1}$

| | Temperature | Conversion based on C4-olefins | ISO index |
|---|---|---|---|
| Catalyst 2 (noninventive) | 80° C. | 32.6% | 1.11 |
| | 90° C. | 38.3% | 1.10 |
| | 100° C. | 40.6% | 1.08 |

In contrast to catalyst 2 which has a ratio of tetrahedrally coordinated aluminium to octahedrally coordinated aluminium of about 65:35, the ratio for the catalyst according to the invention is 95:5. It has surprisingly been found that this makes it possible to achieve a discernible enhancement in conversion in the case of approximately constant ISO indices.

The invention claimed is:

1. An oligomerization catalyst comprising nickel oxide, an Al-free and Si-containing binder and an amorphous silica-alumina support material, wherein the catalyst has a composition of from 15% to 40% by weight of NiO, from 5% to 20% by weight of $Al_2O_3$, from 55% to 80% by weight of $SiO_2$ and 0.01% to 1% by weight of an alkali metal oxide, wherein the oligomerization catalyst has a ratio of tetrahedrally coordinated framework aluminium atoms to octahedral coordinated framework aluminium atoms of 75:25 to 100:0, determined by $^{27}$Al MAS NMR.

2. The oligomerization catalyst according to claim 1, wherein the oligomerization catalyst has a specific BET surface area of from 150 to 400 m$^2$/g, determined by nitrogen physisorption.

3. The oligomerization catalyst according to claim 1, wherein the oligomerization catalyst has mesopores and macropores.

4. The oligomerization catalyst according to claim 3, wherein the mesopores of the oligomerization catalyst have an average pore diameter of from 5 to 15 nm determined by mercury porosimetry.

5. The oligomerization catalyst according to claim 3, wherein the macropores of the oligomerization catalyst have an average pore diameter of from 1 to 100 µm determined by mercury porosimetry.

6. The oligomerization catalyst according to claim 1, wherein the oligomerization catalyst is in the form of granulate.

7. The oligomerization catalyst according to claim 1, wherein the oligomerization catalyst has an average particle diameter (d50) of from 0.1 mm to 7 mm, determined by imaging methods according to ISO 13322-1 (2004 Dec. 1 version) and ISO 13322-2 (2006 Nov. 1 version).

8. The oligomerization catalyst according to claim 2, wherein the oligomerization catalyst has mesopores and macropores.

9. The oligomerization catalyst according to claim 2, wherein the oligomerization catalyst is in the form of granulate.

10. The oligomerization catalyst according to claim 2, wherein the oligomerization catalyst has an average particle diameter (d50) of from 0.1 mm to 7 mm, determined by imaging methods according to ISO 13322-1 (2004 Dec. 1 version) and ISO 13322-2 (2006 Nov. 1 version).

* * * * *